United States Patent [19]

Pezzaniti et al.

[11] Patent Number: 5,788,632
[45] Date of Patent: Aug. 4, 1998

[54] APPARATUS AND PROCESS FOR THE NON-INVASIVE MEASUREMENT OF OPTICALLY ACTIVE COMPOUNDS

[75] Inventors: J. Larry Pezzaniti, Round Lake; John M. Lindberg, Grayslake, both of Ill.

[73] Assignee: Abbott Laboratories, Abbott Park, Ill.

[21] Appl. No.: 618,654

[22] Filed: Mar. 19, 1996

[51] Int. Cl.[6] ............................................. A61B 5/00
[52] U.S. Cl. ........................... 600/316; 600/322; 356/368
[58] Field of Search ..................... 128/633, 664, 128/665; 356/39, 364, 366, 368; 600/316, 318, 319, 322, 473, 476

[56] References Cited

U.S. PATENT DOCUMENTS

| | | | |
|---|---|---|---|
| 4,306,809 | 12/1981 | Azzam | 356/368 |
| 4,882,492 | 11/1989 | Schlager . | |
| 4,901,728 | 2/1990 | Hutchinson | 128/633 |
| 5,009,230 | 4/1991 | Hutchinson | 128/633 |
| 5,086,229 | 2/1992 | Rosenthal . | |
| 5,209,231 | 5/1993 | Cote . | |
| 5,218,207 | 6/1993 | Rosenthal . | |
| 5,321,265 | 6/1994 | Block . | |
| 5,337,745 | 8/1994 | Benaron . | |
| 5,361,758 | 11/1994 | Hall . | |
| 5,383,452 | 1/1995 | Buchert . | |
| 5,535,743 | 7/1996 | Backhaus et al. . | |

FOREIGN PATENT DOCUMENTS

| | | |
|---|---|---|
| 42 43 142 | 6/1994 | Germany . |
| 89/11825 | 12/1989 | WIPO . |
| 92/07511 | 5/1992 | WIPO . |
| 9210131 | 6/1992 | WIPO . |
| 9307801 | 4/1993 | WIPO . |
| 9402837 | 2/1994 | WIPO . |
| 9405984 | 3/1994 | WIPO . |
| 9413199 | 6/1994 | WIPO . |

OTHER PUBLICATIONS

J. L. Pezzaniti, "Mueller Matrix Imaging Polarimetry" A Dissertation, pp. 66–89, 132, 133, and 220–223 The Department of Physics of The School of Graduate Studies of the University of Alabama in Huntsville, 1993.

J.L. Pezzaniti, *Mueller matrix imaging polarimetry*, Chp. 2, Ph.D. dissertation, The University of Alabama in Huntsville (1993).

*Primary Examiner*—Jennifer Bahr
*Assistant Examiner*—Eric F. Winakur
*Attorney, Agent, or Firm*—David L. Weinstein; Gregory W. Steele

[57] ABSTRACT

An apparatus and a process of determining the concentration of an optically active compound in a biological sample are provided. The process measures the entire polarization state of the sample and compares the measured polarization state of the sample to the polarization state of a sample having a known concentration of that compound. The polarization state of the sample is measured after manipulating the polarization state of light entering and leaving the sample and detecting the light leaving the sample. The apparatus contains a source of light, a sample holder for holding the biological sample, a detector, a first polarization manipulator between the light source and the sample holder, a second polarization manipulator between the sample holder and the detector and an analyzer to correlate detected signals with concentration of the optically active compound.

45 Claims, 6 Drawing Sheets

APPARATUS AND PROCESS FOR THE NON-INVASIVE MEASUREMENT OF OPTICALLY ACTIVE COMPOUNDS

FIELD OF THE INVENTION

The field of this invention is the non-invasive determination of optically active compounds. More particularly, this invention is directed to an apparatus and process for the non-invasive determination of an optically active compound in a biological sample using the entire polarization state of light passing through the sample.

BACKGROUND OF THE INVENTION

Several spectroscopic techniques have been disclosed which make use of a compound's unique absorption signature at different wavelengths. Knowledge of those absorption, signatures for different compounds is then used to determine their concentration in a sample. By way of example, certain techniques use changes in the polarized light for each compound and knowledge of those changes is then used to identify the concentrations of the compound in an unknown sample. In other techniques, the signal from an unknown is correlated or compared to the signature of a known compound (called correlation spectroscopy).

There are major shortcomings attendant to the use of such general spectrophotometric techniques. First, there is a lack of specificity (several compounds have similar signatures) and the scattering of tissue significantly distorts the signature of the compounds. Second, such spectroscopic methods have problems with signal to noise ratios. Thus, either the measurement method is not specific enough (other compounds interfere) or the accuracy of the measurement is low (noisy or poor quality data).

Despite these shortcomings there have been numerous reports of attempts to adapt such techniques to the non-invasive measurement of optically active compounds in biological samples (e.g., in an organism). In particular, such attempts have focused on the measurement of glucose in various body compartments.

Existing methods for the determination of glucose using changes in the polarization of light are limited because they use only part of the entire polarization state such as optical rotation and/or circular dichroism (See, e.g., International Patent Publications WO 92/10131, WO 93/07801, WO 94/02837, WO 94/05984, and WO 94/13199; U.S. Pat. Nos. 4,882,492, 5,086,229, 5,209,231, 5,218,207, 5,321,265, 5,337,745, 5,361,758, and 5,383,452.)

There continues to be a need to provide a solution to the problems inherent in existing methods by providing a process that uses all of the available information from the entire polarization state of light entering and leaving a sample.

SUMMARY OF THE INVENTION

The present invention provide an apparatus for the non-invasive measurement of an optically active compound in a biological sample. The apparatus comprises a source of unpolarized light, a first means for manipulating the polarization state of light which is optically aligned with the light source, a sample holder for holding the biological sample optically aligned with the first means for manipulating light to pass light through the sample, a second means for manipulating the polarization state of light optically aligned with the sample holder to receive light passing through the sample, means for detecting light optically aligned with the second means for manipulating the polarization state of light, and means for analyzing an electric signal from the means for detecting light to correlate the signal with concentration of the optically active compound.

In one embodiment of this apparatus of the invention the first means for manipulating the polarization state of light includes a first means for polarizing light optically aligned with the light source and a first means for variably retarding light optically aligned with the first means for polarizing light and the sample holder. Preferably, the first means for polarizing light includes a first polarizer and the first means for variably retarding light includes a first variable retarder. Preferably, the second means for manipulating the polarization state of light includes a second means for variably retarding light optically aligned with the sample holder and a second means for polarizing light optically aligned with the second means for variably retarding light and the means for detecting light. Preferably, the second means for variably retarding light includes a second variable retarder and the second means for polarizing light includes a second polarizer. The variable retarder(s) can independently be rotating retarders, such as crystalline or polymer retarders, which optionally include means for regulating their rotation at the same or different angular frequencies.

Alternatively, the variable retarder can include a pair variable retarders (such as liquid crystals) with the fast axis of the first variable retarder oriented at a 45° angle relative to the polarizer and the fast axis of the second retarder oriented parallel to the polarizer.

The invention further provides an apparatus including a data processor and/or controllers associated with the detector and the means for manipulating the polarization states.

The invention also provides an apparatus including one or more light sources (each of which emits light at a particular wavelength(s)), focusing and reflecting elements, means for splitting light, and linear array detectors.

In another aspect, the invention provides a process of determining the concentration of an optically active compound in a biological sample comprising measuring the entire polarization state of the sample and comparing the measured polarization state of the sample to the polarization state of known concentration of that compound.

More particularly, the present invention provides a process wherein the polarization state of the sample is measured after manipulating the polarization state of light entering and/or leaving the sample and detecting the light leaving the sample. Preferably, the frequency, phase and intensity of light leaving the second means for polarizing light is detected and an electric signal generated. The signal may then be correlated with the concentration of the optically active compound in the sample.

The invention also provides a noninvasive process of determining glucose concentration in a biological sample comprising the steps of manipulating the polarization state of a light beam, passing the manipulated light through the sample, manipulating the polarization state of light leaving the sample, detecting the manipulated light leaving the sample, and processing an electric signal generated by the detection of manipulated light into a signal indicative of the concentration of glucose in the sample.

The invention further provides a noninvasive process of determining glucose concentration in a biological sample comprising the steps of sequentially passing a light beam through a first polarization generator, directing light through the sample contained in a sample holder, sequentially passing light from the sample through a second polarization generator, detecting light from the second polarizer with a detector, and processing an electric signal generated by the detector with an analyzer to a signal indicative of the concentration of glucose in the sample.

The invention also provides a polarization generator for introducing polarization states into a sample, comprising a linear polarizer optically aligned with a first variable linear retarder, the first retarder having its fast axis oriented at 45 degrees relative to the transmission axis of the first polarizer, and a second variable retarder optically aligned with the first variable linear retarder and having the fast axis of the second retarder oriented parallel to the transmission axis of the linear polarizer.

In a further process of the invention, the Mueller matrix of a optically active compound in a sample can be measured by optically aligning the sample with the beam generated by the polarization generator of the invention, detecting light from the sample and processing an electric signal generated by the detector with an analyzer to indicate the concentration of optically active compound in the sample.

The invention further provides a polarization analyzer for analysis of polarization states of a sample, comprising a first variable linear retarder having its fast axis oriented at a 45° angle relative to the polarizer and the fast axis of the second retarder oriented parallel to the polarizer.

Also provided is a process for measuring the Mueller matrix of a sample comprising optically aligning a sample with the optical beam generated by the polarization generator of the invention, optically aligning the polarization analyzer of the invention with the light exiting the sample, transmitting light through the polarization generator, the sample and the polarization analyzer, and detecting light from the sample and processing an electric signal generated by the detector with an analyzer to indicate the concentration of optically active compound in the sample.

A further process of the invention provides for measuring circular retardance of a sample, comprising optically aligning a sample with the polarization generator of the invention, optically aligning a fixed linear polarizer with the light exiting the sample, optically aligning a detector with the light exiting the fixed linear polarizer, and detecting light from the sample and processing an electric signal generated by the detector with an analyzer to indicate the concentration of optically active compound in the sample.

An additional process of the invention provides for measuring the circular dichroism of a sample, comprising optically aligning a sample with the polarization generator of the invention, transmitting light through the polarization generator and the sample, and detecting light from the sample and processing an electric signal generated by the detector with an analyzer to indicate the concentration of optically active compound in the sample.

Yet a further process of the invention provides for measuring a Mueller matrix, circular retardance or circular dichroism using multiple wavelengths.

A further process of the invention provides for reducing the Mueller matrix of a sample wherein the reduction is selected from horizontal linear diattenuation, 45 degree linear diattenuation, circular diattenuation, horizontal linear retardance, 45 degree linear retardance, circular retardance, or depolarization.

The preferred optically active compound for detection in the apparatus and processes of the invention is glucose; the preferred biological sample is a fluid sample, or for the noninvasive methods of the invention, a finger, earlobe, eye, eyelid, or aqueous humor of an eye.

BRIEF DESCRIPTION OF THE DRAWINGS

In the drawings, which form a portion of the specification.

DETAILED DESCRIPTION

The present invention provides an apparatus and process for non-invasively measuring the concentration of an optically active compound in a biological sample using changes in the entire polarization state of light as it interacts with the sample.

The processes of the invention involve measuring the entire polarization state of the sample and comparing the measured polarization state of the sample to the polarization state of a sample having a known concentration of that compound, i.e., a standard.

As used herein, the phrase "noninvasive" means that a process of the present invention can be carried out on an organism without invading that organism. In other words, a process can be used to measure the concentration of an optically active compound in a sample of that organism without removing that sample from the organism or without inserting any instrumentation into the organism.

Optically active compounds are well known in the art to represent compounds that alter the wavelength, phase or intensity of light illuminating that sample. The manner and particular spectrum of light affected by optically active compounds are also well known to a skilled artisan.

As used herein, the term "light" means electromagnetic radiation, preferably in the range of 100 nm to 20 µm, more preferably 400 nm to about 10 µm.

In a preferred embodiment, the optically active compound is glucose. In accordance with this embodiment, the present invention therefore provides a non-invasive process of determining glucose concentration in a biological sample.

That process comprises the steps of manipulating the polarization state of a light beam, passing the manipulated light through the sample, manipulating the polarization state of light leaving the sample, detecting the frequency, phase and intensity of the manipulated light leaving the sample, processing an electric signal generated by the detection of manipulated light into a signal indicative of the concentration of glucose in the sample.

Existing methods for determining glucose concentration only use measurements of the optical rotation and circular dichroism of a sample. As is described in more detail below, those aspects are only part of the information available from the polarization state of light.

The present process is particularly suited to the measurement of analytes contained in various body fluid compartments. An especially preferred analyte is glucose. Glucose is known to alter certain characteristics of light in the near-infrared (NIR) wavelength range, e.g., in the range of about 400 nm to about 1800 nm.

In accordance with the present process, light of known polarization state is generated and directed at the sample of interest. The wavelength of that light includes wavelengths known to be affected by the particular compound whose concentration is being determined. However, the optically active compound in the sample modifies the polarization state of the light. This modified light is analyzed and detected with optics that measure a known polarization state. The polarization state of the source and detector are changed and the measurement is made again. This is repeated until the entire polarization state is determined.

The entire polarization state of the sample is measured after manipulating the polarization state of light entering and/or leaving the sample and detecting the light leaving the sample. A useful polarization manipulator is as follows. A linear polarizer oriented at 0 degrees (defining a global coordinate system) is followed by a variable retarder, e.g., liquid crystal, electro-optic modulator or some other variable retarder, with its fast axis oriented at forty five degrees relative to the linear polarizer. The variable retarder is followed by a second variable retarder with its fast axis oriented parallel to the transmission axis of the polarizer. One advantage of this polarization manipulator is that it does not require moving optical elements. This manipulator has an additional advantage in that it is straightforward to modulate at a rate much faster than the pulsatile frequency. The polarization state of light entering the sample may also be manipulated by sequentially passing light through a first polarizer and a first variable retarder (such as those previously described) before entering the sample. The polarization state of light leaving the sample is manipulated by sequentially passing light through a second variable retarder and a second polarizer.

Data is collected on the compound or compounds of interest to determine the relationship between the change in the polarization state and the compound of interest. By using the knowledge of these relationships, a determination of concentration can be made by the measurement of an unknown sample.

Any biological sample can be used in the above-described process by configuring an apparatus for measuring concentration such that a sample holder positions the sample in the beam of light. In a preferred embodiment, a sample is a body fluid sample and the sample holder is configured to receive a portion of the organism known to contain that sample. Exemplary and preferred body parts are fingers, ear lobes and eyes. Means for configuring optical devices for receiving such body portions are well known in the art.

The polarization state of the sample is measured after manipulating the polarization state of light entering and leaving the sample. The frequency, phase and intensity of light leaving the sample are then detected.

In accordance herewith, the polarization state of light entering the sample is manipulated by sequentially passing light through a first polarizer and a first variable retarder before entering the sample. The polarization state of light leaving the sample may then be manipulated by sequentially passing light through a second variable retarder and a second polarizer.

The frequency, phase and intensity of light leaving the second means for polarizing light is detected and an electric signal generated. This electric signal is correlated with the concentration of the optically active compound in the sample.

As will now be apparent to those skilled in the art, the above-described process uses all of the information contained in the Mueller matrix for determining the effect the sample has upon the light. The Mueller matrix is a recognized mathematical method for describing the polarization change a sample imparts to light. The Mueller representation is more general than the other representations because it works with partially polarized light and can be used to describe scattering media.

The Mueller matrix contains seven or sixteen degrees of freedom depending on whether the optical system is non-polarizing or polarizing. To complete the Mueller matrix 16 measurements are needed. There is no known way to directly measure the elements of the matrix. There are several well known methods for making the measurements and for converting the measurements into the Mueller matrix elements (See, e.g., Azzam and Bashara "Ellipsometry and Polarized Light", North Holland Physics Publishing, 1977).

The Mueller matrix can be decomposed (a polar decomposition is performed on the matrix) to provide a complete description of the polarization altering characteristics of a sample. A sample can display three types of polarization altering characteristics: (1) diattenuation—the dependence of intensity transmittance (reflectance) on incident polarization state, (2) retardance—the dependence of the phase (optical path length) of a beam exiting on polarization state, and (3) depolarization—a process which couples polarized light into unpolarized light. Depolarization is intrinsically associated with scattering and with diattenuation and retardance which vary in space, time, and/or wavelength. Diattenuation, retardance and depolarization can be further decomposed into more specific types of polarization characteristics. Diattenuation has three degrees of freedom. These degrees of freedom are typically referred to as horizontal linear, 45 degree linear, and circular diattenuation. Horizontal (45 degree linear) refer to a difference in attenuation between horizontal (45 degree) linear polarization states and the orthogonal linear polarization state. Circular diattenuation (a phenomena also described in terms of circular dichroism) is defined as the difference in attenuation between right circularly polarized light and left circularly polarized light. Similarly, retardance has three degrees of freedom with horizontal linear, 45 degree linear, and circular components. Depolarization, in general, has nine degrees of freedom.

Compounds of interest (in particular glucose) may display all three possible polarization altering characteristics, retardance diattenuation and depolarization. A single molecule can display linear birefringence and linear diattenuation, as well as circular retardance and circular diattenuation. A solution of a large number of the same molecules, however, will not display linear retardance or linear diattenuation, unless some long range orientational order is imposed on the molecules. For a solution with a collection of molecules in random orientations, the linear diattenuation and the linear retardance contributions of individual molecules will average to zero. The circular components of retardance and diattenuation, on the other hand will increase with concentration and optical path length.

A Mueller matrix of e.g., blood, tissue, or aqueous humor in the eye, will contain polarization contributions from the compound of interest, the surrounding medium, and other compounds. The components of polarization from the measurements must be separated so that the polarization signature of the component of interest may be discerned. For example, if the Mueller matrix associated with light propagating through the cornea is measured, there will be polarization contributions from the glucose, the cornea walls, cholesterol molecules, and other compounds. The result is a mixing of the polarization signatures from each of the components, causing an interference in the intended signal.

The Mueller matrix decomposition allows the interfering contributions to be removed from the signal. Unless the polarization contribution of the surrounding medium can be separated from the desired polarization signature, the measurement will be a function of measurement location on the body. Small changes in surrounding medium polarization will yield spurious measurements of compound concentrations.

Algorithms to separate a Mueller matrix into its components currently exist. Given an arbitrary Mueller matrix, a polar decomposition may be performed on the matrix to determine the linear and circular diattenuation (3 numbers), the linear and circular retardance (3 numbers), and the depolarization index (1 number, although as many as nine numbers may be available).

The measurements described above can be simplified to measure specific portions of the Mueller matrix, as opposed to the full Mueller matrix. The measurement procedure can be designed such that it is most sensitive to a particular form of polarization, either retardance, diattenuation or depolarization. What follows are two embodiments of the process of the invention which are sensitive to changes in optical rotation (circular retardance), and circular dichroism (circular diattenuation).

A protocol which is sensitive to circular retardance can be described as follows. If a sample displays only circular retardance, the sample will display the following properties with respect to polarization. First, when circularly polarized light is introduced to the sample, circularly polarized light will exit the sample unchanged. When linearly polarized light is introduced into the sample, the orientation of the linearly polarized light exiting the sample will be rotated by an angle equaling half of the magnitude of the circular retardance. For example a circular retarder with 180 degrees of retardance will rotate the linearly polarized incident beam by 90 degrees. Thus this embodiment of the invention measures the rotation in a linearly polarized beam, involving a least squares fit to a large data set.

The polarization generator of this system remains identical to the system described previously for measuring Mueller matrices, but the variable retarders are removed from the polarization analyzer. The second variable retarder is set to 90 degrees and the first retarder is cycled between 0 and 180 degrees. The function of the polarization generator is to produce linearly polarized light that varies in orientation from 0 to 180 degrees as a function of time. If the sample is removed, then the intensity of the light incident on the detector will vary sinusoidally in time as the orientation of the incident linearly polarized light varies from 0 to 180 degrees. The period of this oscillation will be half the period of the polarization generator. In other words, as orientation of linear polarization from the polarization generator varies from 0 to 180 degrees, the sinusoid at the detector will undergo a half period of oscillation. If a sample is inserted which has optical rotation, the phase of the sinusoid will be shifted by an amount equaling half of the sample's circular retardance.

This process of the invention can be calibrated to account for small variations in the retardance in the variable retarders so that multiple wavelengths can be used.

A protocol which is sensitive to circular dichroism can be described as follows. This embodiment of the process of the invention measures the differential absorption between right and left circularly polarized light. The optical system is the same as the one for measuring optical rotation, except that the polarizer before the detector is removed. The first variable retarder is set to 90 degrees, to convert the linearly polarized beam from the source to circularly polarized light. The second variable retarder is used to convert a right circularly polarized beam to left circularly polarized light. The second variable retarder is set to zero retardance then stepped to 180 degrees of retardance. Thus the optical system measures the transmittance of right circularly polarized light then left circularly polarized light. Several measurements of the transmittance of these two states are measured to increase the signal to noise.

The Mueller matrix can be decomposed into three simpler Mueller matrices, each describing an individual polarization form: diattenuation, depolarization and retardance.

Consider a Mueller matrix M, with terms given by $$M = \begin{bmatrix} m_{00} & m_{01} & m_{02} & m_{03} \\ m_{10} & m_{11} & m_{12} & m_{13} \\ m_{20} & m_{21} & m_{22} & m_{23} \\ m_{30} & m_{31} & m_{32} & m_{33} \end{bmatrix}$$

The effect of a retarder on an incident polarization state represented on the Poincare sphere is equivalent to a rotation about the fast axis with an angle identical to the retardance. Thus, the following matrix $$M_R = \begin{bmatrix} 1 & 0 & 0 & 0 \\ 0 & r_1^2(1-\cos\delta)+\cos\delta & r_1 r_2(1-\cos\delta)+r_3\sin\delta & r_1 r_3(1-\cos\delta)-r_2\sin\delta \\ 0 & r_1 r_2(1-\cos\delta)-r_3\sin\delta & r_2^2(1-\cos\delta)+\cos\delta & r_2 r_3(1-\cos\delta)+r_1\sin\delta \\ 0 & r_1 r_3(1-\cos\delta)+r_2\sin\delta & r_2 r_3(1-\cos\delta)-r_1\sin\delta & r_3^2(1-\cos\delta)+\cos\delta \end{bmatrix}$$

is the most general Mueller matrix for a retarder with the retardance $\delta$ and fast axis at $[1,r_1,r_2,r_3]^T$. Note that $r_1^2+r_2^2+r_3^2=1$. For instance, letting $[1,r_1,r_2,r_3]^T$ equal $[1,1,0,0]$, $[1,0,1,0]$, or $[1,0,0,1]$ one derives horizontal, 45 deg. linear, and circular retarders respectively.

The above expression for $M_R$ provides a way to derive the Mueller matrix of the retarder with given fast axis and retardance. Furthermore, this expression determines the fast axis orientation and retardance magnitude given a pure retarder Mueller matrix $$\delta = \cos^{-1}\left[\frac{1}{2} Tr[M] - 1\right],$$

$r_1 = (m_{23} - m_{32})/(2 \sin \delta)$ $r_2 = (m_{31} - m_{13})/(2 \sin \delta)$ $r_3 = (m_{12} - m_{21})/(2 \sin \delta).$ A diattenuator has a Mueller matrix which is symmetric. The most general Mueller matrix for a diattenuator is $$M_D = \begin{bmatrix} 1 & d_1 & d_2 & d_3 \\ d_1 & \sqrt{1-D^2} + (1-\sqrt{1-D^2})\frac{d_1^2}{d_1^2+d_2^2+d_3^2} & (1-\sqrt{1-D^2})\frac{d_1d_2}{d_1^2+d_2^2+d_3^2} & (1-\sqrt{1-D^2})\frac{d_1d_3}{d_1^2+d_2^2+d_3^2} \\ d_2 & (1-\sqrt{1-D^2})\frac{d_2d_1}{d_1^2+d_2^2+d_3^2} & \sqrt{1-D^2}+(1-\sqrt{1-D^2})\frac{d_2^2}{d_1^2+d_2^2+d_3^2} & (1-\sqrt{1-D^2})\frac{d_2d_3}{d_1^2+d_2^2+d_3^2} \\ d_3 & (1-\sqrt{1-D^2})\frac{d_3d_1}{d_1^2+d_2^2+d_3^2} & (1-\sqrt{1-D^2})\frac{d_3d_2}{d_1^2+d_2^2+d_3^2} & \sqrt{1-D^2}+(1-\sqrt{1-D^2})\frac{d_3^2}{d_1^2+d_2^2+d_3^2} \end{bmatrix}$$

where $D=\sqrt{d_1^2+d_2^2+d_3^2}$ is the diattenuation magnitude, and $d_1$, $d_2$ and $d_3$ represent the horizontal, 45 deg. linear and circular components of diattenuation. The diattenuation matrix has the complete information regarding the diattenuation magnitude and orientation of a sample, $$d_1 = \frac{m_{01}}{m_{00}}$$

$$d_1 = \frac{m_{02}}{m_{00}}$$

$$d_1 = \frac{m_{03}}{m_{00}}$$

$$D = \sqrt{d_1^2 + d_1^2 + d_1^2} = \frac{\sqrt{m_{01}^2 + m_{02}^2 + m_{03}^2}}{m_{00}}$$

From a polar decomposition of a Mueller matrix, any non-depolarizing Mueller matrix can be expressed as a diattenuator followed by a retarder $$M = M_R M_D.$$

It follows that a retarder Mueller matrix $M_R$ can be computed from $$M_R = MM_D^{-1},$$

with the assumption that $M_D$ is non-singular. If $M_D$ is singular, it means that the sample is an ideal diattenuator (perfect polarizer). In this case retardance is not defined, and its Mueller matrix is not uniquely determined.

For a depolarizing Mueller matrix, the operation $MM_D^{-1}$ does not yield a pure retarder. Further steps must be taken which are described below. First, construct a matrix M' given by $$M' = MM_D^{-1},$$

where M' contains both retardance and depolarization information. Without loss of generality, M' can be written as a retarder Mueller matrix followed by a depolarizing Mueller matrix, $$M' = M_{dp}M_R,$$

where $M_{dp}$ is a pure depolarizing Mueller matrix. It follows that the depolarizing Mueller matrix must be symmetric, reducing its degrees of freedom to nine, and the depolarizing Mueller matrix has neither diattenuation nor retardance. From these relationships the reduction in the degree of polarization of an incident polarization state can be separated from the diattenuation and the retardance. Further details of this calculation are described in *Mueller matrix imaging polarimetry*, Chapter 2, J. L. Pezzaniti, Ph.D. dissertation, The University of Alabama in Huntsville (1993).

In another aspect, the present invention provides an apparatus for the non-invasive measurement of an optically active compound in a biological sample.

One embodiment of such an apparatus contains a source of unpolarized light, a first polarization manipulator optically aligned with the light source, and a sample holder for holding the biological sample optically aligned with the first polarization manipulator. A second polarization manipulator optically aligned with the sample holder, a light detector optically aligned with the second polarization manipulator, and an analyzer to correlate signals from the detector with concentration of the optically active compound are also included in one embodiment of that apparatus.

Figure 1:
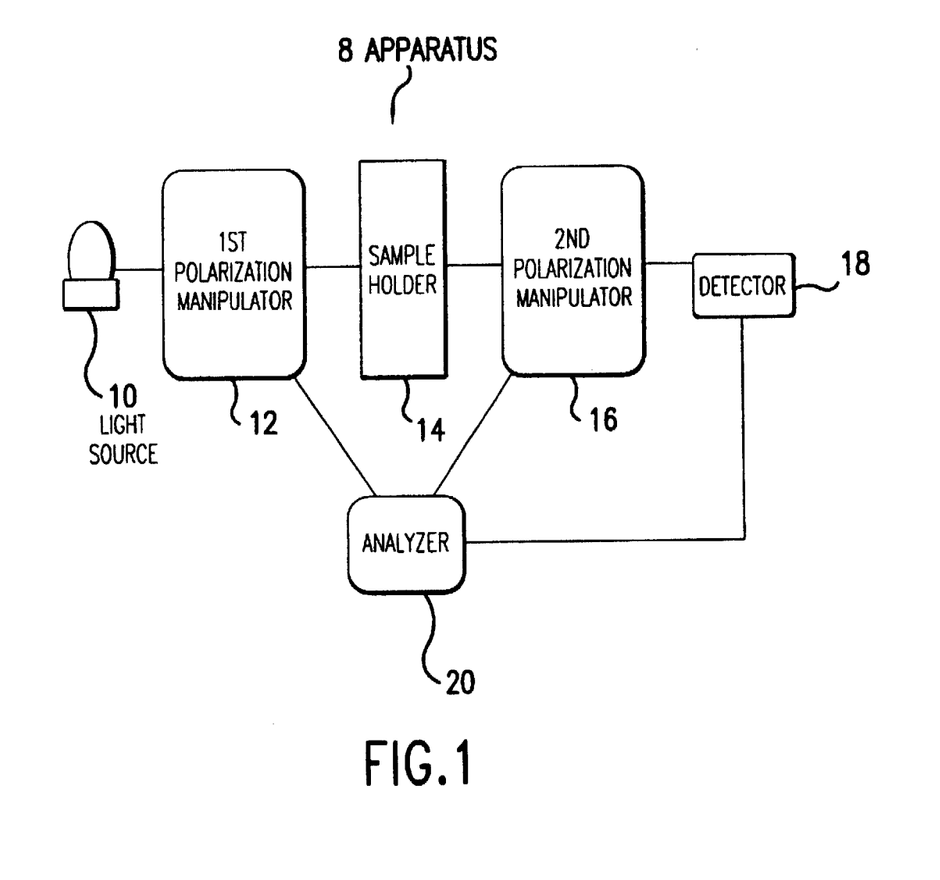
FIG. 1 is a schematic drawing of a first embodiment of an apparatus of the present invention.

A schematic drawing of such an apparatus 8 is illustrated in FIG. 1. Referring to FIG. 1, apparatus 8 includes a light source 10 coupled to and energized by a power supply (not shown). In the embodiment shown in FIG. 1, the light source provides polychromatic light.

Sources of polychromatic light are well known in the art. An exemplary light source is a tungsten-halogen filament lamp. Any polychromatic light source that provides light containing a wavelength range known to be affected by the compound under study can be used without departing from the spirit and scope of the present invention.

In other embodiments to be disclosed hereinafter, the light source can be a light emitting diode (LED) or laser that emits light at a particular wavelength. Light emitted from light source 10 is unpolarized. The unpolarized light leaving light source 10 is spatially coherent or collimated.

After leaving light source 10, the unpolarized light passes through a first polarization manipulator 12. First polarization manipulator 12 is optically aligned with light source 10 so as to receive the collimated, unpolarized light from light source 10.

The polarization manipulator 12 is a combination of optical elements that alters the polarization state of light. Optical elements that can be included in such a manipulator include diattenuators, polarizers and retarders.

Light from first polarization manipulator 12 is directed to a sample holder 14 for holding the biological sample during measurement. The sample holder is configured for non-invasive measurements of a portion of the human body such as a finger.

Sample holder 14 is positioned such that it is optically aligned with first polarization manipulator 12. With this alignment, the biological sample (e.g., finger) receives light passing through manipulator 12.

The apparatus further includes a second polarization manipulator 16 optically aligned with sample holder 14. The manipulator 16 receives light passing through the sample contained within sample holder 14.

After passing through second manipulator 16, light is directed to a detector 18 that detects the frequency, phase, and intensity of light emerging from the sample. The detector 18 is optically aligned with second manipulator 16 so as to receive light from that second manipulator 16.

The detector 18 generates an electrical signal that is sent to an analyzer 20. The analyzer 20 in a preferred embodiment is a digital, programmed data processor that processes an electric signal from detector 18. In response thereto, analyzer 20 generates a signal indicative of the concentration of the optically active compound in the sample. Analog analysis circuitry could be used as an alternate to digital circuitry.

Analyzer 20 is also electronically connected to first 12 and second 16 manipulators to regulate the manipulation of polarization.

One advantage of the present invention is the use of a detector 18 that detects and measures all those elements of light necessary to describe the entire polarization state of light entering it. A detector is complete if it measures the sample's full Mueller matrix, and is incomplete otherwise.

To use the entire polarization state of light (i.e., to complete the measurements necessary for use of the Mueller Matrix) it is necessary that the first 12 and second 16 polarization manipulators manipulate the polarization and retardance of light.

Polarization refers to the orientation of light with respect to its propagation direction. Polarization can be linear, circular or elliptical. For linear polarization, the polarization states with maximum and minimum transmittance or reflectance are linear. For circular polarization, the corresponding polarization states are circular, and for elliptical polarization the associated polarization states are elliptical.

Retardance is the difference in phase accumulation (optical path length) between the two eigenpolarization states of a polarization element. The accumulated phase for one eigenpolarization state is a maximum and is a minimum for the other eigenpolarization state.

A polarization manipulator alters the polarization and retardance of light through the use of polarizers and retarders. A schematic drawing of an apparatus 8-1 employing such devices is illustrated in FIG. 2.

Figure 2:
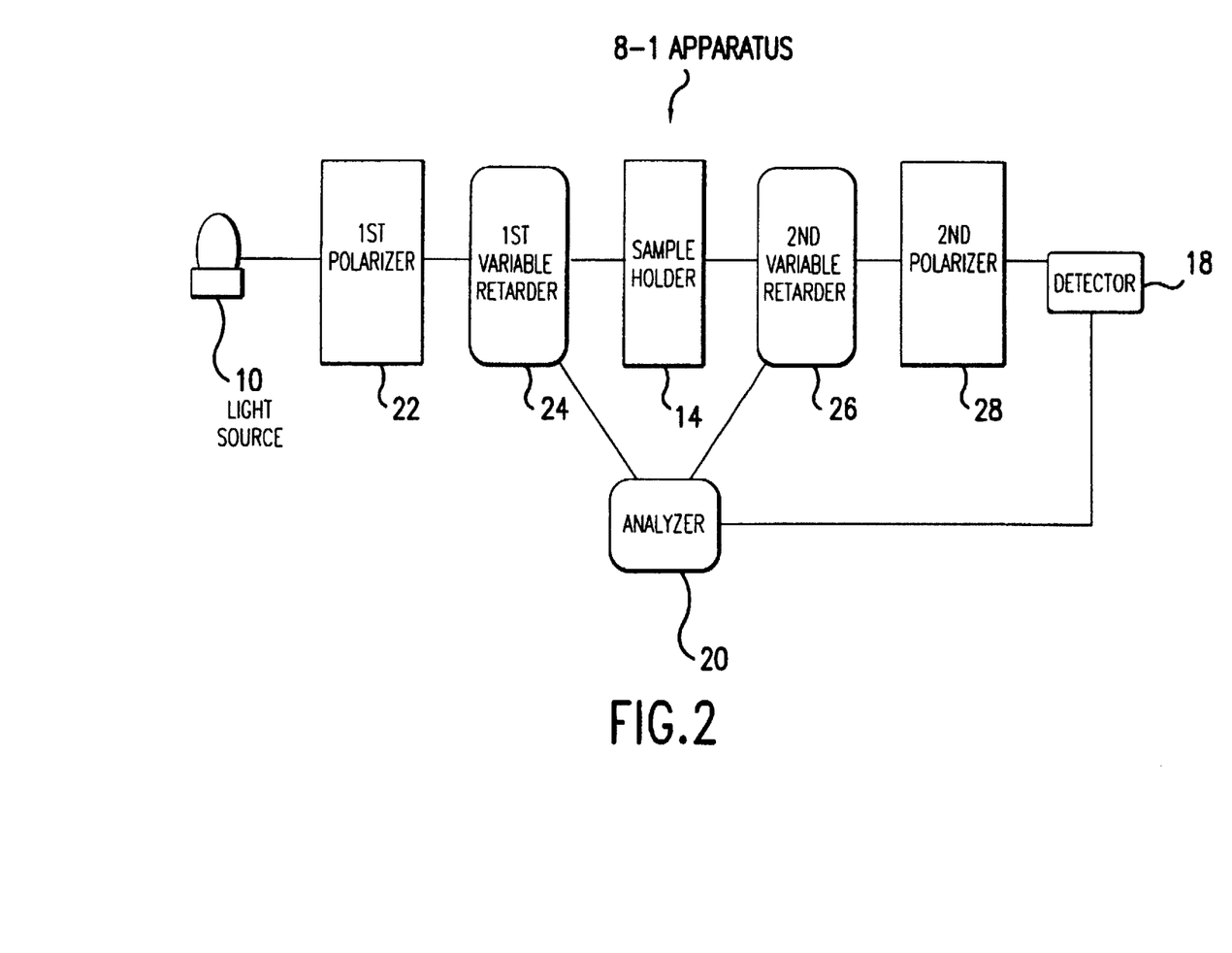
FIG. 2 is a schematic drawing of a second embodiment of an apparatus of the present invention.

With reference to FIG. 2, the first polarization manipulator 12 includes a first polarizer 22 that is optically aligned with light source 10. Light passing through first polarizer 22 is directed to a first variable retarder 24.

First variable retarder 24 is optically aligned with first polarizer 22. Light leaving first variable retarder 24 is directed to the sample contained in sample holder 14.

With further reference to FIG. 2, it can be seen that the second polarization manipulator 16 includes a second variable retarder 26 optically aligned with sample holder 14 and a second polarizer 28 optically aligned with second variable retarder 26.

Both first 22 and second 28 polarizers are linear and preferably stationary polarizers. Such a linear polarizer can be any crystal or polaroid polarizer with a high extension coefficient that linearly polarizes light passing through it.

First 24 and second 26 variable retarders may be fixed or rotating retarders. In a preferred embodiment, both the first and second variable retarders are fixed and are electronically connected to analyzer 20 to control the frequency of rotation of those retarders. The details of this preferred embodiment has been previously described. Alternatively, the first retarder may be fixed and the second retarder rotating. In this embodiment, the rotating retarder is mounted on a rotary stage and electronically connected to the analyzer as described previously.

Regulation of the rotation frequency of the first and second rotary retarders is such that they can be rotated at different angular frequencies. In one embodiment, a second rotating retarder can be rotated at a frequency greater than the angular frequency of rotation of the first rotating retarder. In such an embodiment, it is preferred that the second rotating retarder is rotated at a frequency five times that of the angular frequency of rotation of the first rotating retarder.

A known retarder is the waveplate, a parallel plate of birefringent material, with the crystal axis oriented perpendicular to the direction of propagation. Waveplates are often made from a practical thickness of a durable birefringent material such as crystalline quartz.

Due to the high birefringence of quartz, a quarter- or half-wave retarder from a single layer is only possible with a very thin layer of quartz. One alternative to cleaving very thin plates is to use a practical thickness of quartz and obtain a multiple-order waveplate, say 15.5 waves of retardance for 1 mm thickness.

Such a plate will behave exactly the same as a half-wave plate. However, as the optical wavelength is changed, the retardation will change much more rapidly than it would for a true half-wave plate. Similarly, the sensitivity of the retardation about the fast and slow axes is much larger than a true half-wave plate.

In yet another aspect, an apparatus in accordance with the present invention can additionally contain focusing elements to direct light within apparatus 8. Such an embodiment 8-2 is schematically shown in FIG. 3.

Figure 3:
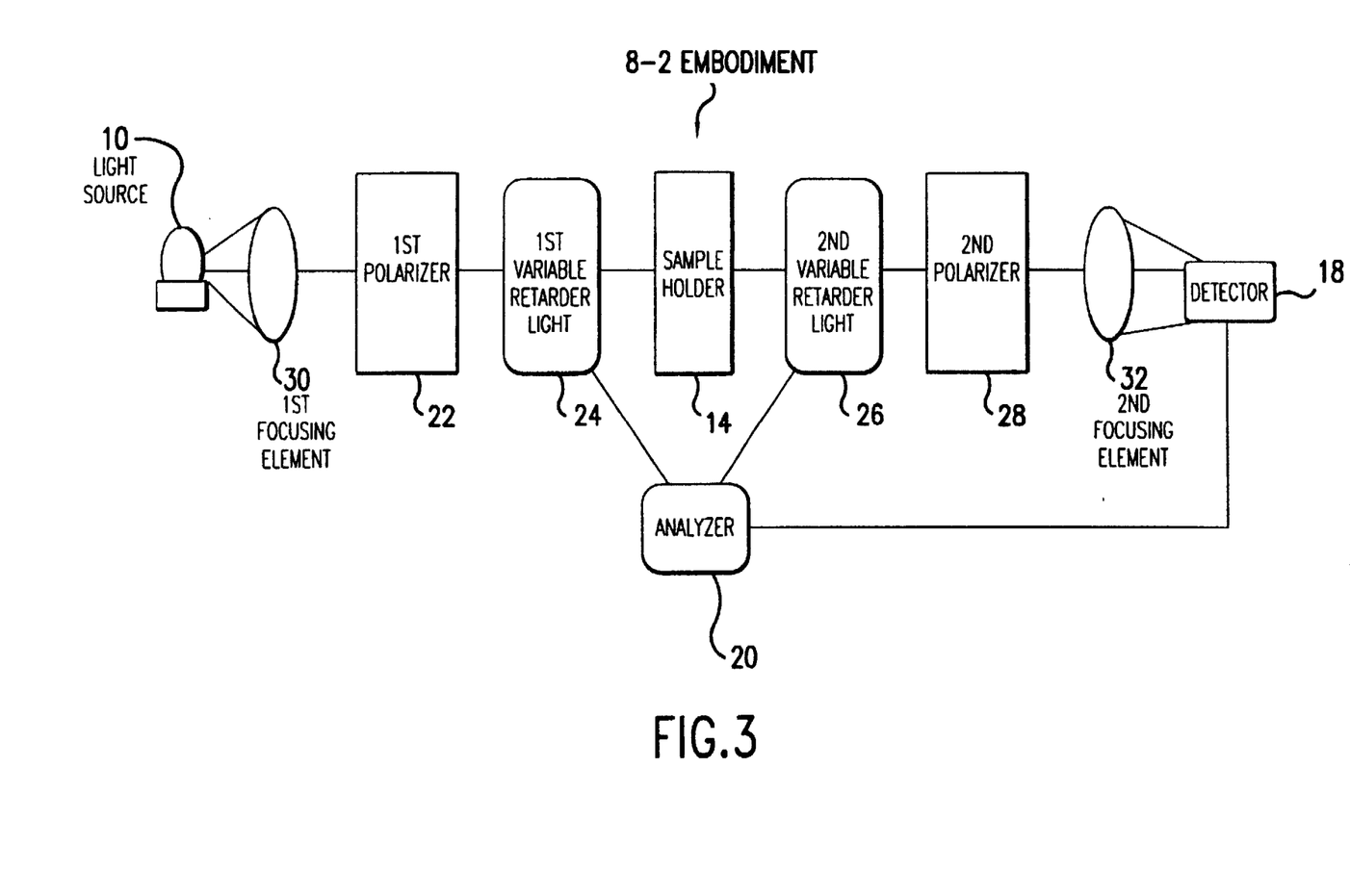
FIG. 3 is a schematic drawing of a third embodiment of an apparatus of the present invention.

As shown in FIG. 3, a first focusing element 30 is positioned between light source 10 and first polarizer 22. Focusing element 30 is optically aligned with light source 10 and first polarizer 22 to focus and direct light leaving light source 10 on the first polarizer 22. Similarly, second focusing element 32 is positioned between second polarizer 28 and detector 18 to focus light leaving second polarizer 28 upon detector 18.

Figure 5:
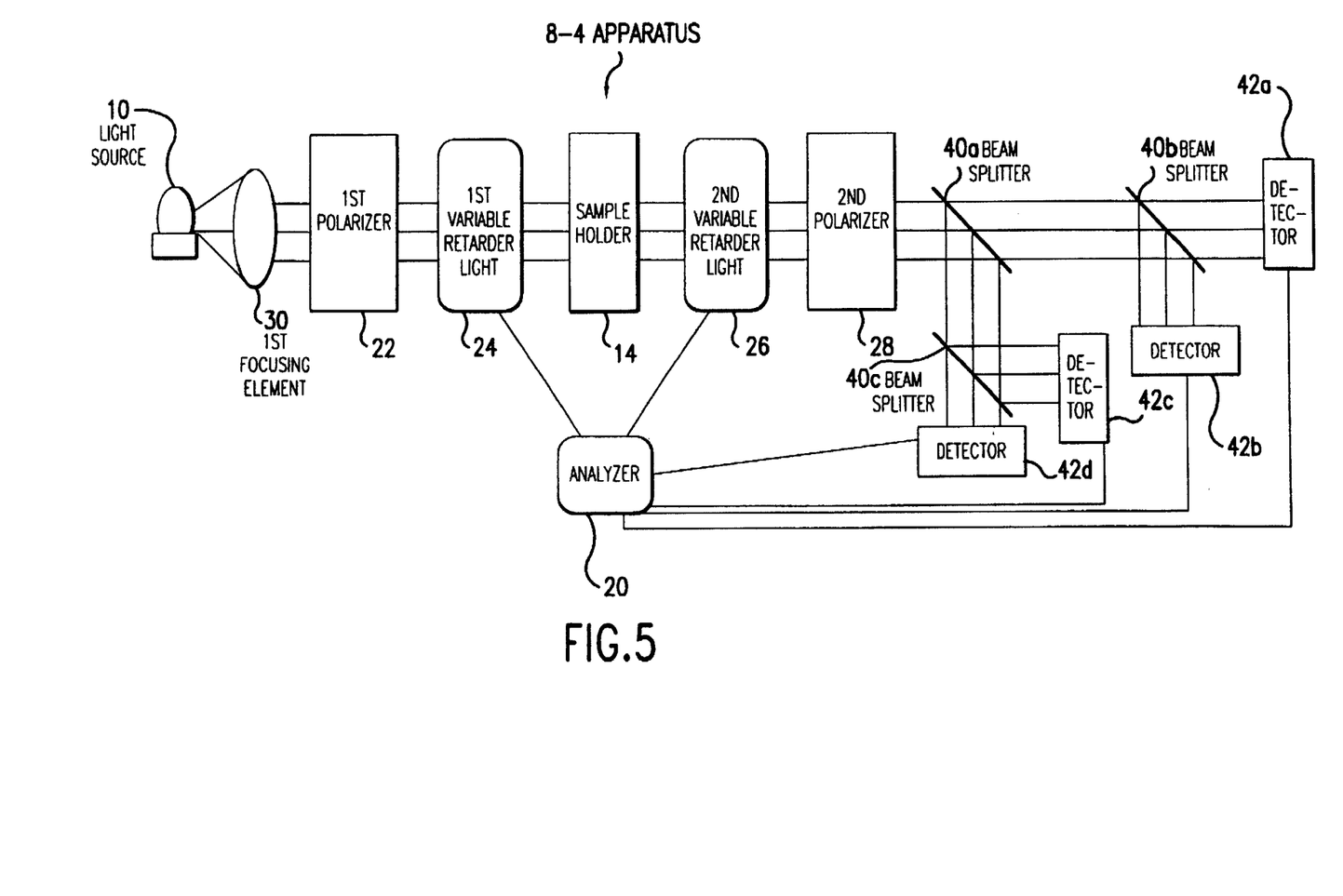
FIG. 5 is a schematic drawing of a fifth embodiment of an apparatus of the present invention.
Figure 6:
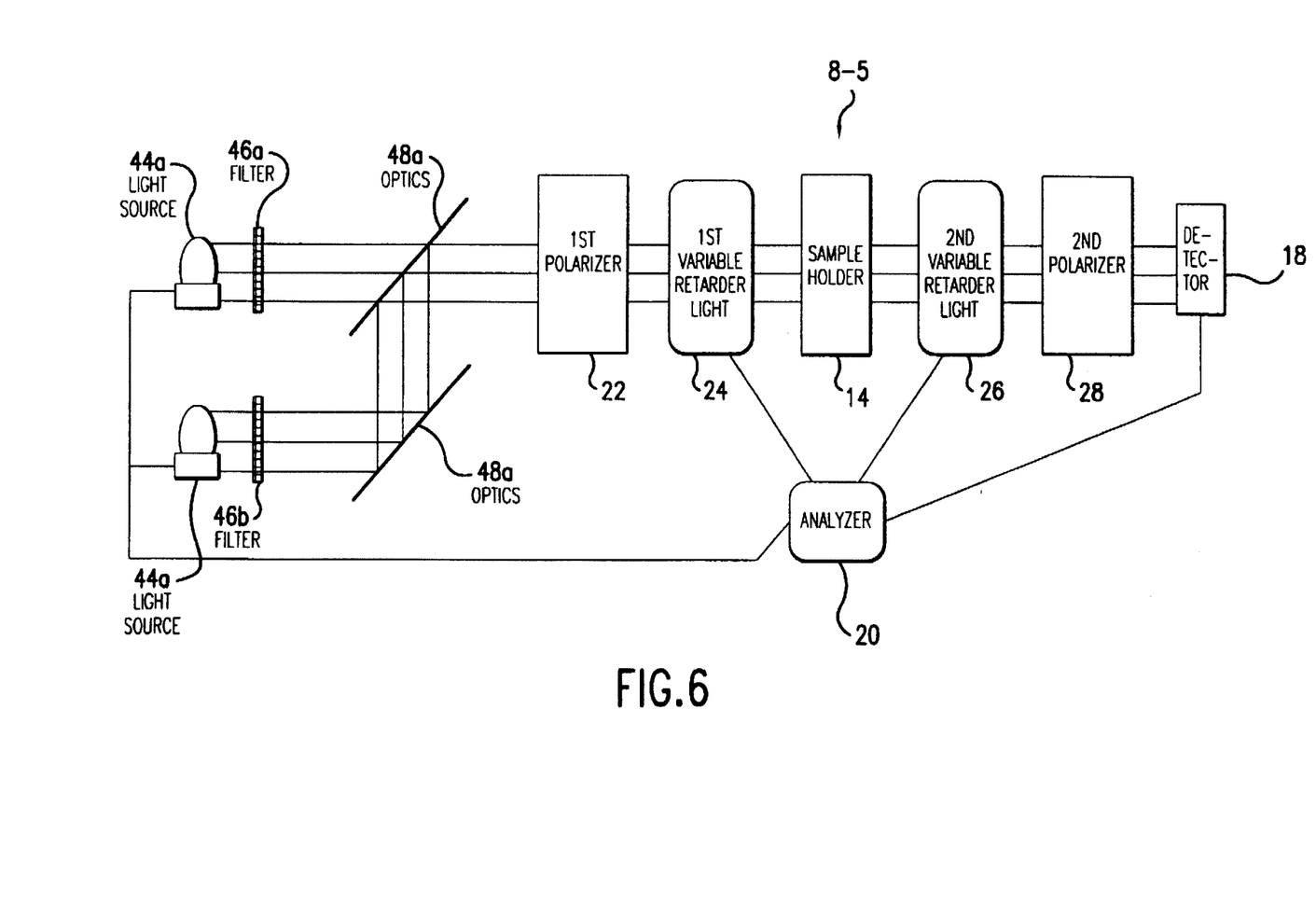
FIG. 6 is a schematic drawing of a sixth embodiment of an apparatus of the present invention.

In the embodiments shown in FIGS. 1–3, the described apparatus uses a single source of light and a single detector structures. An apparatus can also employ multiple light sources with a single detector or a single source of light with multiple detectors. Such embodiments are illustrated in FIGS. 4, 5 and 6.

In accordance with one such embodiment, manipulated light emerging from the sample is dispersed into discrete wavelengths and each of those discrete wavelengths is individually detected. A polychrometer can be used to accomplish this function.

Thus, another embodiment of an apparatus in accordance with the present invention can include a beam splitter light optically aligned with the second focusing element and a dispersive element optically aligned and positioned between the beam splitter light and the detector. In this case, the detector includes a plurality of linear array detectors.

Figure 4:
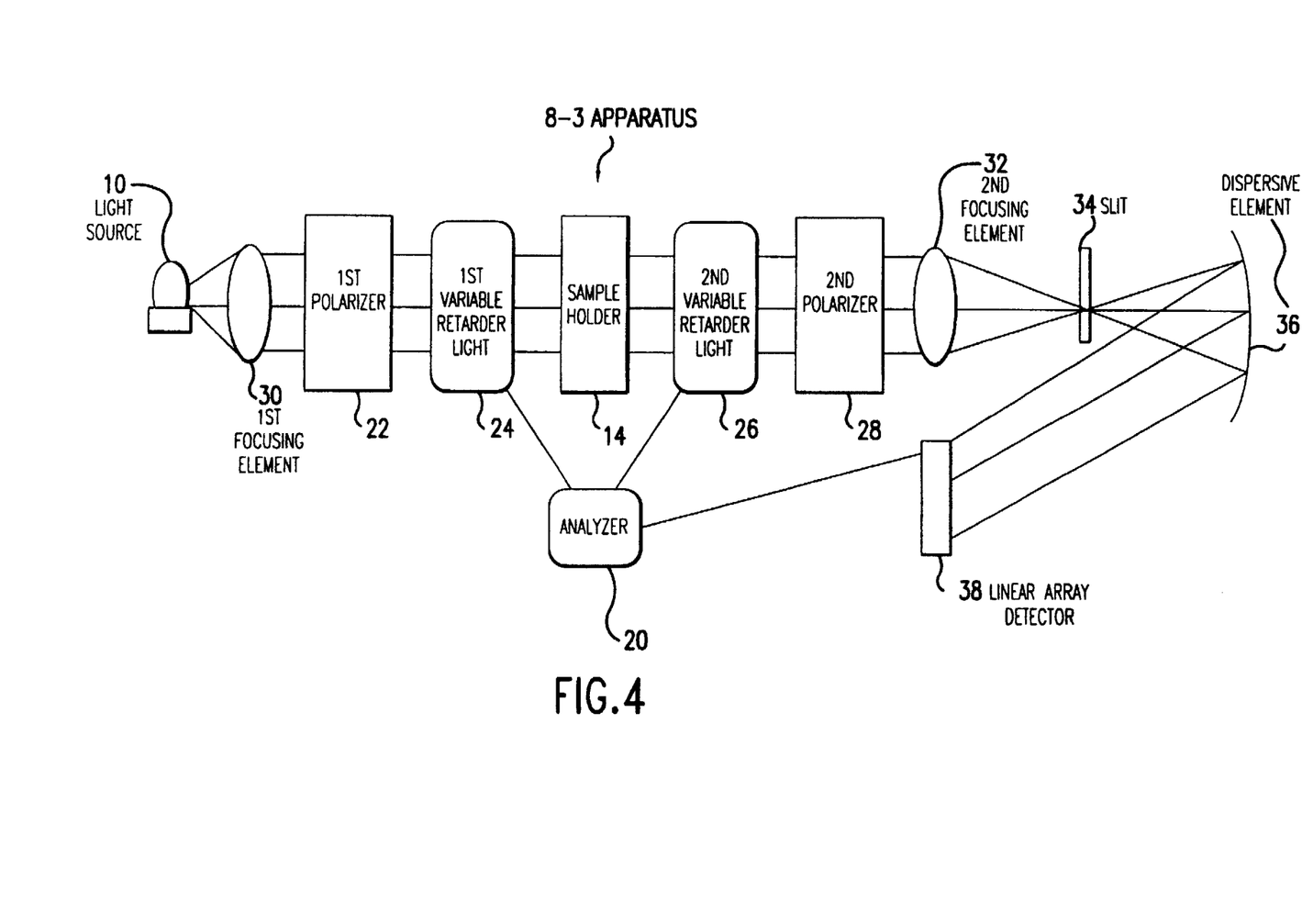
FIG. 4 is a schematic drawing of a fourth embodiment of an apparatus of the present invention.

An embodiment of such an apparatus 8-3 is schematically illustrated in FIG. 4. The apparatus of FIG. 4 includes a light source 10, a first focusing element 30, a first polarizer 22, a first variable retarder light 24, a sample holder 14, a second variable retarder 26, a second polarizer 28, and a second focusing element 32, all as set forth above in FIG. 3.

In accordance with the use of a polychrometer, focused light leaving second focusing element 32 is passed through a slit 34. Light leaving slit 34 is then directed to dispersive element 36 where the light is separated into its individual wavelength spectra.

Light separated into its spectra is directed from dispersive element 36 to linear array detector 38. Linear array detector 38 measures the intensity of light at each wavelength for a given polarization state. As is the case with other embodiments, the first and second polarizers and the first and second variable retarders are used to generate specific polarization states.

One of ordinary skill in the art can readily envision equivalent structures to slit 34, dispersive element 36 and linear detector array 38. The dispersive element can be a grating, a hologram or a prism. The polychrometer can also be replaced with a scanning monochrometer and a single detector.

In still yet another embodiment, an apparatus in accordance with the present invention can utilize multiple discrete wavelength detectors. A schematic illustration of an apparatus 8-4 in accordance therewith is set forth in FIG. 5. In this embodiment, light is manipulated as in FIG. 4. However, in the apparatus 8-4, instead of detecting light with a polychrometer, light is detected with several discrete detectors each of which are sensitive to only part of the detected wavelength range.

Thus, in FIG. 5, light leaving second polarizer 28 is directed to a plurality of beam splitters 40a–c, which beam splitters 40 direct light to individual detectors 42a–d. Each of detectors 42a–d is sensitive to a discrete region of the measured wavelength range. Each of individual detectors 42a–d is electronically coupled to analyzer 20.

In another embodiment, multiple light sources are used, each of which light sources provides light at a particular wavelength range. Such an apparatus includes a plurality of discrete light sources, each of which emits light at a particular wavelength. Preferably, such an apparatus further includes a plurality of filtering elements and a plurality of routing optics. In further accordance with this embodiment, a single detector is used.

A schematic drawing of such an embodiment 8-5 is shown in FIG. 6. In the apparatus 8-5 illustrated in FIG. 6, a single light source is replaced by a plurality of discrete light sources 44a–b. In a preferred embodiment, those discrete light sources are light-emitting diodes (LED), laser diodes or lasers.

Light leaving discrete light sources 44a–b is passed through filtering elements 46a–b that are optically aligned with discrete light sources 44a–b. Light passing through filtering elements 46a–b is then directed to first polarizer 22. The light path from first polarizer 22 to detector 18 is the same as set forth above.

Light leaving filtering elements 46a–b is directed to first polarizer 22 using routing optics 48a–b. Exemplary such routing optics are reflective or reflective/transmissive devices such as silvered mirrors.

The present invention has been described with reference to preferred embodiments. Those embodiments are not limiting of the claims and specification in any way. One of ordinary skill in the art can readily envision changes, modifications and alterations to those embodiments that do not depart from the scope and spirit of the present invention.

What is claimed is:

1. An apparatus for the non-invasive measurement of an optically active component in a biological sample comprising:

a) a source of unpolarized light;
  b) a first means for manipulating the polarization state of light in optical alignment with the light source;
  c) a sample holder adapted to hold the biological sample in optical alignment with the first means for manipulating light to allow light to pass through the sample, wherein the first means for manipulating the polarization state of light includes a first means for polarizing light optically aligned with the light source and a first means for variably retarding light optically aligned with the first means for polarizing light and the sample holder, wherein the first means for polarizing light includes a first polarizer and the first means for variably retarding light includes a first variable retarder, wherein the first variable retarder contains a pair of variable retarders with the fast axis of the first retarder of the pair being oriented about 45° to the fast axis of the second retarder of the pair;
  d) a second means for manipulating the polarization state of light in optical alignment with the sample holder to receive light passing through the sample;
  e) means for detecting light in optical alignment with the second means for manipulating the polarization state of light; and
  f) means for analyzing an electric signal from the means for detecting light to correlate the electric signal with a concentration of the optically active compound.

2. The apparatus of claim 1 wherein the first variable retarder is a rotating retarder.

3. The apparatus of claim 1 wherein the second means for manipulating the polarization state of light includes a second means for variably retarding light optically aligned with the sample holder and a second means for polarizing light optically aligned with the second means for variably retarding light and the means for detecting light.

4. The apparatus of claim 3 wherein the second means for variably retarding light includes a second variable retarder and the second means for polarizing light includes a second polarizer.

5. The apparatus of claim 4 wherein the second variable retarder includes a rotating retarder.

6. The apparatus of claim 5 wherein the first and second variable retarders are rotating retarders.

7. The apparatus of claim 6 further comprising a means for regulating the rotation of the rotating retarders operatively associated with the rotating retarders.

8. The apparatus of claim 7 wherein the means for regulating the rotation of the rotating retarders includes means for rotating the rotating retarders simultaneously at different angular frequencies.

9. The apparatus of claim 5 wherein both the first and second variable retarders consist of a pair of variable retarders with the fast axis of the first retarder of the pair oriented about 45° to the fast axis of the second retarder of the pair.

10. The apparatus of claim 9 wherein a means for regulating retardance of the first and second variable retarders is operatively associated with the first and second variable retarders.

11. The apparatus of claim 10 wherein the means for regulating retardance of the first and second variable retarders includes a means for changing the retardance simultaneously at different frequencies.

12. The apparatus of claim 4 wherein the second means for variably retarding light contains a pair of variable retarders with the fast axis of the first retarder of the pair oriented about 45° to the fast axis of the second retarder of the pair.

13. The apparatus of claim 1 wherein the means for analyzing includes a data processor operatively associated with the means for detecting and a controller operatively associated with the first and second means for manipulating polarization states.

14. The apparatus of claim 1 further comprising first means for focusing light positioned between the light source and the first means for manipulating the polarization state of light and second means for focusing light positioned between the second means for manipulating the polarization state of light and the means for detecting light.

15. The apparatus of claim 14 further comprising means for splitting light optically aligned with the second means for focusing light and a means for dispersing light optically aligned and positioned between the means for splitting light and the means for detecting light.

16. The apparatus of claim 15 wherein the means for detecting light includes a plurality of linear array detectors.

17. The apparatus of claim 1 wherein the light source includes a plurality of discrete light sources, each of which emits light at a particular wavelength.

18. The apparatus of claim 17 further comprising a plurality of means for filtering light, each of which is optically aligned with one of said discrete light sources.

19. The apparatus of claim 18 further comprising a plurality of means for reflecting light, each of which is optically aligned with one of the means for filtering light and positioned to direct light from the filtering means to the first means for manipulating the polarization state of light.

20. A process of determining the concentration of an optically active compound in a biological sample comprising the steps of:

measuring the entire polarization state of the sample, and comparing the measured polarization state of the sample to the polarization state of a sample having a known concentration of that compound, wherein the polarization state of the sample is measured after the polarization state of light entering the sample is manipulated and the polarization state of light leaving the sample is manipulated and the light leaving the sample is detected.

21. The process of claim 20 wherein the polarization state of light entering the sample is manipulated by sequentially passing light through a first means for polarizing light and a first means for variably retarding light before entering the sample.

22. The process of claim 21 wherein the polarization state of the light leaving the sample is manipulated by sequentially passing the light through a second means for variably retarding light and a second means for polarizing light.

23. The process of claim 22 wherein the frequency, phase, and intensity of the light leaving the second means for polarizing light is detected and an electric signal is generated.

24. The process of claim 23 wherein the electric signal is correlated with the concentration of the optically active compound in the sample.

25. The process of claim 20 wherein the optically active compound is glucose.

26. A noninvasive process of determining glucose concentration in a biological sample comprising the steps of:

a) sequentially passing a light beam through a first polarizer and a first variable retarder, wherein the first variable retarder contains a pair of variable retarders with the fast axis of the first retarder of the pair being oriented about 45° to the fast axis of the second retarder of the pair;

b) directing the light beam through the sample contained in a sample holder;

c) sequentially passing light from the sample through a second variable retarder and a second polarizer;

d) detecting the light from the second polarizer with a detector; and e) processing an electric signal generated by the detector with an analyzer to a signal indicative of the concentration of glucose in the sample.

27. The process of claim 26 wherein the sample is a finger, earlobe, eye, eyelid, or aqueous humor of an eye.

28. A polarization generator for introducing polarization states into a sample, comprising:

a linear polarizer, a first variable retarder having its fast axis oriented at 45° relative to the transmission axis of the polarizer, c) a second variable retarder in optical alignment with the first variable retarder and having the fast axis of the second retarder oriented parallel to the transmission axis of the linear polarizer.

29. A process for measuring the Mueller matrix of a sample comprising the steps of optically aligning a sample with an optical beam generated by the polarization generator of claim 28, detecting the light emerging from the sample, and processing an electric signal generated by the detected light with an analyzer to indicate the concentration of an optically active compound in the sample.

30. The process of claim 29 wherein the sample is a finger, earlobe, eye, eyelid, or aqueous humor of an eye.

31. A polarization analyzer for analysis of polarization sates of a sample, comprising:

a) a first variable retarder optically aligned with a sample holder, b) a second variable retarder having its fast axis oriented at 45° relative to the fast axis of the first linear retarder, optically aligned with the sample holder, c) a linear polarizer having its transmission axis oriented parallel to the fast axis of the first variable retarder.

32. A process for measuring the Mueller matrix of a sample, comprising the steps of:

a) transmitting light through the polarization generator of claim 28, said polarization generator aligned with the sample, b) transmitting said light transmitted through the polarization generator through the sample, and c) transmitting the light transmitted through the sample through the polarization analyzer of claim 31, the polarization analyzer being in optical alignment with the light transmitted through the sample and parallel to the light transmitted through the polarization generator.

33. The process of claim 32, wherein multiple wavelengths are used.

34. The process of claim 32, further including the step of reducing the Mueller matrix of the sample, wherein the step of reducing is selected from the group consisting of horizontal linear diattenuation, 45° linear diattenuation, circular diattenuation, horizontal linear retardance, 45° linear retardance, circular retardance, or depolarization.

35. The process of claim 34 wherein the sample is a finger, earlobe, eye, eyelid, or aqueous humor of an eye.

36. The process of claim 34, wherein the step of reducing is selected from the group consisting of horizontal linear diattenuation, 45° linear diattenuation, and circular diattenuation.

37. The process of claim 34, wherein the step of reducing is selected from the group consisting of horizontal linear retardance, 45° linear retardance, and circular retardance.

38. The process of claim 34, wherein the step of reducing is depolarization.

39. The process of claim 32 wherein the sample is a finger, earlobe, eye, eyelid, or aqueous humor of an eye.

40. A process for measuring circular retardance of a sample, comprising the steps of:
   a) transmitting light through the polarization generator of claim 28, said polarization generator aligned with the sample,
   b) transmitting said light transmitted through the polarization generator through the sample, and
   c) transmitting the light transmitted through the sample through the polarization analyzer of claim 31, the polarization analyzer being in optical alignment with the light transmitted through the sample and parallel to the light transmitted through the polarization generator, said polarization analyzer having variable retarders removed therefrom.

41. The process of claim 40 wherein the sample is a finger, earlobe, eye, eyelid, or aqueous humor of an eye.

42. The process of claim 40, wherein multiple wavelengths are used.

43. A process for measuring circular dichroism of a sample, comprising the steps of:
   a) transmitting light through the polarization generator of claim 32, said polarization generator aligned with the sample,
   b) transmitting said light transmitted through the polarization generator through the sample, and
   c) transmitting the light transmitted through the sample through the polarization analyzer of claim 31, the polarization analyzer being in optical alignment with the light transmitted through the sample and parallel to the light transmitted through the polarization generator, said polarizer preceding said detector being removed.

44. The process of claim 43 wherein the sample is a finger, earlobe, eye, eyelid, or aqueous humor of an eye.

45. The process of claim 43, wherein multiple wavelengths are used.

* * * * *

UNITED STATES PATENT AND TRADEMARK OFFICE
CERTIFICATE OF CORRECTION

PATENT NO. : 5,788,632
DATED : August 4, 1998
INVENTOR(S) : Pezzaniti et al.

It is certified that error appears in the above-identified patent and that said Letters Patent is hereby corrected as shown below:

Column 16, line 10, insert an a) at beginning of sentence.

Column 16, line 11, insert a b) at beginning of sentence.

Signed and Sealed this

Sixteenth Day of February, 1999

Attest:

*Acting Commissioner of Patents and Trademarks*

*Attesting Officer*